(12) United States Patent
Molloy

(10) Patent No.: US 6,245,578 B1
(45) Date of Patent: *Jun. 12, 2001

(54) ANALYTICAL APPARATUS

(75) Inventor: James Oscar Molloy, Newmarket (GB)

(73) Assignee: Fisons PLC (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,658

(22) Filed: Feb. 23, 1998

Related U.S. Application Data

(63) Continuation of application No. 08/549,728, filed as application No. PCT/GB94/01161 on May 27, 1994, now Pat. No. 5,770,462.

(30) Foreign Application Priority Data

| May 28, 1993 | (GB) | 9311073 |
| Oct. 19, 1993 | (GB) | 9321570 |

(51) Int. Cl.[7] .................... G01N 33/552; G01N 33/553
(52) U.S. Cl. ............. 436/527; 356/426; 356/427; 356/428; 385/12; 385/129; 385/130; 422/50; 422/55; 422/58; 422/82.05; 422/82.11; 435/287.1; 435/287.2; 435/288.7; 435/808; 436/164; 436/165; 436/527; 436/535; 436/518; 436/805; 436/524; 436/525
(58) Field of Search ................. 356/426–428; 385/12, 129, 130; 422/50, 55, 58, 82.05, 82.11; 435/287.1, 287.2, 288.7, 808; 436/164, 165, 527, 535, 518, 805, 524, 525

(56) References Cited

U.S. PATENT DOCUMENTS

| 3,869,215 | 3/1975 | Nolan | 356/246 |
| 4,125,327 | * 11/1978 | Margolis . | |
| 4,978,503 | * 12/1990 | Shanks et al. | 435/288 |
| 5,051,551 | * 9/1991 | Doyle . | |
| 5,085,759 | * 2/1992 | Harker . | |
| 5,170,056 | * 12/1992 | Berard et al. . | |
| 5,770,462 | * 6/1998 | Molloy | 356/427 |

FOREIGN PATENT DOCUMENTS

| 0 205 236 | * 12/1986 | (EP) . |
| 0 262 760 | * 4/1988 | (EP) . |
| 62-168045 | * 7/1987 | (JP) . |

OTHER PUBLICATIONS

X. Wu, D. Ripple, and C. Franck, "Growth of a wetting layer in a flowing binary–liquid mixture at bulk coexistance", Physical Review A: General Physics, 36 (1987) Oct. 15, No. 8, 3$^{rd}$ Series, New York, NY, USA, pp. 3975–3983.*

* cited by examiner

Primary Examiner—Christopher L. Chin
(74) Attorney, Agent, or Firm—Nixon Peabody LLP

(57) ABSTRACT

An analytical apparatus comprises a biosensor device (3) which forms the base of a sample chamber. A stirrer (8) extends into the sample chamber and moves within the chamber so as to homogenize a sample contained within the chamber in contact with the biosensor (3). Movement of the stirrer (8) is preferably reciprocal movement along an axis perpendicular to the surface of the biosensor (3).

20 Claims, 6 Drawing Sheets

ANALYTICAL APPARATUS

This application is a continuation of Ser. No. 08/549,728 filed Feb. 20, 1996 now U.S. Pat. No. 5,770,462 which is a PCT GB/94/01161 filed May 27, 1994.

This invention relates to analytical apparatus for the qualitative or quantitative determination of chemical or biochemical species or their interactions.

Many devices for the automatic determination of biochemical analytes in solution have been proposed in recent years. Typically, such devices (biosensors) include a sensitised coating layer which is located in the evanescent region of a resonant field. Detection of the analyte typically utilizes optical techniques such as, for example, surface plasmon resonance (SPR), and is based on changes in the thickness and/or refractive index of the coating layer resulting from interaction of that layer with the analyte. This causes a change, eg in the angular position of the resonance.

Other optical biosensors include a waveguide in which a beam of light is propagated. The optical characteristics of the device are influenced by changes occurring at the surface of the waveguide. One form of optical biosensor is based on frustrated total reflection. The principles of frustrated total reflection (FTR) are well known; the technique is described, for example, by Bosacchi and Oehrle [Applied Optics (1982), 21, 2167–2173]. An FTR device for use in immunoassay is disclosed in European Patent Application No 0205236A and comprises a cavity layer bounded on one side by the sample under investigation and on the other side by a spacer layer which in turn is mounted on a substrate. The substrate-spacer layer interface is irradiated with monochromatic radiation such that total reflection occurs, the associated evanescent field penetrating through the spacer layer. If the thickness of the spacer layer is correct and the incident parallel wave vector matches one of the resonant mode propagation constants, the total reflection is frustrated and radiation is coupled into the cavity layer. The cavity layer must be composed of material which has a higher refractive index than the spacer layer and which is transparent at the wavelength of the incident radiation.

In all such devices, problems can occur due to thermal effects. For accurate results it is vital to ensure that the sample reaches good equilibration with the surroundings and that comparative measurements are carried out at constant temperatures. In addition, inhomogeneities or transport phenomena occurring within the sample may lead to difficulties.

There has now been devised an analytical apparatus which overcomes or substantially mitigates the above-mentioned disadvantages.

According to the invention, there is provided an analytical apparatus comprising a biosensor device, a sample chamber adjacent the biosensor device, a stirrer extending into the sample chamber, and means for causing the stirrer to move within the sample chamber.

The apparatus according to the invention is advantageous primarily in that the motor-driven stirrer provides virtually instantaneous homogeneity and uniformity of the samples, in terms of both composition and temperature. This enables a larger area of sensitised coating to be used, which in turn leads to higher sensitivity. The apparatus offers significant advantages compared to known systems in which the sample chamber is a flow cell into which the sample is pumped, since in such systems the reaction kinetics are strongly dependent upon, and often adversely influenced by, the flow hydrodynamics.

The apparatus according to the invention is useful in the qualitative or quantitative determination of an analyte species in a sample or their interactions. The apparatus may be used not only for the determination of the presence and/or concentration of a particular molecular species, but also to monitor any process in which the molecular species interacts with the surface of the biosensor or with other molecular species at or in the vicinity of the surface. For example, the parameter under investigation may be the binding affinity of a molecular species with the biosensor surface.

Generally, the stirrer will comprise an elongate stirrer shaft. The shaft may terminate at a point within the sample chamber which, in use, lies within the sample fluid. Alternatively, the shaft may be connected to a further component which intrudes into the sample chamber.

The means for causing the stirrer to move within the sample chamber is preferably an electric or electromagnetic motor. For some applications, eg applications in which particularly high frequencies are required, piezoelectric devices may be suitable.

The movement imparted to the stirrer may be rotary movement. In such a case, the portion of the stirrer which is, in use, immersed in the sample is preferably provided with a suitable paddle element. The paddle element may take any form suitable for causing effective homogenisation of the sample. Most preferably, the paddle element rotates in a plane parallel to the sensitised surface of the biosensor device. The clearance between the paddle element and the sensitised surface is preferably less than 1 mm, more preferably less than 0.5 mm, eg about 0.2 mm.

Preferably, however, the stirrer is not a rotary stirrer but a stirrer which vibrates. Most preferably, the motion of the stirrer is reciprocal, eg along an axis essentially perpendicular to the sensitised surface of the biosensor.

Again, the portion of the stirrer which, in use, is immersed in the sample is preferably provided with a suitable element to facilitate mixing of the sample. In one preferred embodiment, such an element takes the form of a hollow truncated cone, the top and bottom faces of which are open.

The means for imparting reciprocating motion to the stirrer element are preferably electromagnetic. Most preferably, the upper end of the stirrer shaft is rigidly connected to a former on which is wound a wire coil. The former surrounds a permanent magnet such that when an alternating current is applied to the coil the former, and hence the shaft, oscillate at the frequency of the applied current.

In order to hold the former in position, and to limit the extent of the reciprocating movement, the shaft/former assembly is preferably secured to a flexible membrane which is held in a fixed position relative to the magnet.

The frequency of reciprocation of the stirrer element is typically of the order of a few tens to a few hundred Hertz. The frequency may, for example, be up to about 250 Hz, typically 100–150 Hz.

The stirrer element preferably reciprocates over a distance of less than ±1 mm, more preferably less than ±0.5 mm. The rest position of the stirrer element is preferably such that the separation of the stirrer element from the sensitised surface of the biosensor device, at the point of closest approach, is less than 0.5 mm. For example, the rest position may be 0.5 mm above the surface and the extent of the reciprocal motion may be ±0.3 mm so that the stirrer element oscillates between extreme positions 0.2 mm and 0.8 mm above the surface.

It is particularly preferred that the stirrer element should be capable of being switched off, if desired, at any stage of the measurement process ie the movement of the stirrer element should be capable of being stopped. It is also preferred that the rest position and/or amplitude of modulation and/or frequency of movement of the stirrer element should be adjustable to suit the particular sample under investigation.

It is preferred that the sample chamber forms part of a disposable cuvette.

The cuvette, or at least that part of the cuvette adjacent to the sample chamber, is preferably of a material with high thermal conductivity.

By "high thermal conductivity" is meant sufficient conductivity to provide rapid transfer of heat from a supporting body against which the cuvette is placed. Suitable materials include metals.

Preferably, the cuvette body is of aluminium, more preferably aluminium with an inert coating such as electroless nickel, a fluorocarbon, or a silicon lacquer. In such a case the coating may be of the order of 25 $\mu$m in thickness.

The body is preferably provided with wings or flanges which provide intimate thermal contact with a temperature-controlled block on the analytical apparatus, the relatively large surface area of the wings or flanges providing for rapid thermal equilibration between the block and the body. For the same purpose the analytical apparatus preferably comprises clamping means for holding the cuvette in firm contact with the block.

Thus, according to another aspect of the invention there is provided a sample cuvette comprising a body of material with high thermal conductivity, the body defining a sample chamber with a base incorporating a sensitive surface of a biosensor device, and the body being provided with integrally formed wings or flanges by which the cuvette may be held in intimate thermal contact with a support.

The cuvette preferably includes one or more reserve fluid wells for maintaining a supply of sample or analytical reagents at the measuring temperature.

The volume of the sample chamber is preferably small, eg less than 500 $\mu$l, and most preferably 100–300 $\mu$l.

The arrangement is preferably such that the thermal capacity of the cuvette is considerably greater than that of the fluid in the sample chamber.

The cuvette may contain more than one sample chamber. Such chambers may be completely separate compartments, or may be formed in a single well with suitable partitions.

An advantage of the use of such a cuvette is that it may be readily removed from the analytical apparatus and replaced. A range of cuvettes containing biosensors adapted for different types of measurement may therefore be used, switching from one type of measurement to another being readily accomplished.

The biosensor device is preferably an FTR sensor. Such a sensor will generally include an optical structure comprising a) a cavity layer of transparent dielectric material of refractive index $n_3$, b) a dielectric substrate of refractive index $n_1$, and c) interposed between the cavity layer and the substrate, a dielectric spacer layer of refractive index $n_2$.

In use, the interface between the substrate and the spacer layer is irradiated with light such that internal reflection occurs. Resonant propagation of a guided mode in the cavity layer will occur, for a given wavelength, at a particular angle of incidence of the exciting radiation.

The angular position of the resonant effect depends on various parameters of the sensor device, such as the refractive indices and thicknesses of the various layers. In general, it is a prerequisite that the refractive index $n_3$ of the cavity layer and the refractive index $n_1$ of the substrate should both exceed the refractive index $n_2$ of the spacer layer. Also, since at least one mode must exist in the cavity to achieve resonance, the cavity layer must exceed a certain minimum thickness.

The cavity layer is preferably a thin-film of dielectric material. Suitable materials for the cavity layer include silicon nitride, hafnium dioxide, zirconium dioxide, titanium dioxide, aluminium oxide and tantalum oxide.

The cavity layer may be prepared by known techniques, eg vacuum evaporation, sputtering, chemical vapour deposition, plasma-enhanced or plasma-impulse chemical deposition, or in-diffusion.

The dielectric spacer layer must have a lower refractive index than both the cavity layer and the substrate. The layer may, for example, comprise an evaporated or sputtered layer of magnesium fluoride. In this case an infra-red light injection laser may be used as light source. The light from such a source typically has a wavelength around 600–800 nm. Other suitable materials include lithium fluoride and silicon dioxide. Apart from the evaporation and sputtering techniques mentioned above, the spacer layer may be deposited on the substrate by a sol-gel process, or be formed by chemical reaction with the substrate.

The sol-gel process is particularly preferred where the spacer layer is of silicon dioxide.

The refractive index of the substrate ($n_1$) must be greater than that ($n_2$) of the spacer layer but the thickness of the substrate is generally not critical.

By contrast, the thickness of the cavity layer must be so chosen that resonance occurs within an appropriate range of coupling angles. The spacer layer will typically have a thickness of the order of several hundred nanometers, say from about 200 nm to 2000 nm, more preferably 500 to 1500 nm, eg 1000 nm. The cavity layer typically has a thickness of a few tens of nanometers, say 10 to 200 nm, more preferably 30 to 150 nm, eg 100 nm.

It is particularly preferred that the cavity layer has a thickness of 30 to 150 nm and comprises a material selected from silicon nitride, hafnium dioxide, zirconium dioxide, titanium dioxide, tantalum oxide and aluminium oxide, and the spacer layer has a thickness of 500 to 1500 nm and comprises a material selected from magnesium fluoride, lithium fluoride and silicon dioxide, the choice of materials being such that the refractive index of the spacer layer is less than that of the cavity layer.

Preferred materials for the cavity layer and the spacer layer are silicon nitride and silicon dioxide respectively.

At resonance, the incident light is coupled into the cavity layer by FTR, propagates a certain distance along the cavity layer, and couples back out (also by FTR). The propagation distance depends on the various device parameters but is typically of the order of 1 or 2 mm.

At resonance the reflected light will undergo a phase change, and it is this which may be detected. Alternatively, as described in International Patent Application No WO 92/03720 the cavity layer and/or spacer layer may absorb at resonance, resulting in a reduction in the intensity of the reflected light.

For use in the determination of biochemical species, the surface of the biosensor device, ie the surface of the cavity layer in the case of an FTR sensor, will generally be sensitised by having biomolecules, eg specific binding partners for the analyte(s) under test, immobilised upon it. The immobilised biochemicals may be covalently bound to the sensor surface by methods which are well known to those skilled in the art.

As described in International Patent Application No WO 92/21976, the biosensor may be coated with a layer of a biocompatible porous matrix of, for example, dextran within which suitable binding molecules may be immobilised.

The invention will now be described in greater detail, by way of illustration only, with reference to the accompanying drawings, in which FIG. 1 is a partial schematic diagram of an analytical apparatus according to the invention;

Figure 1:
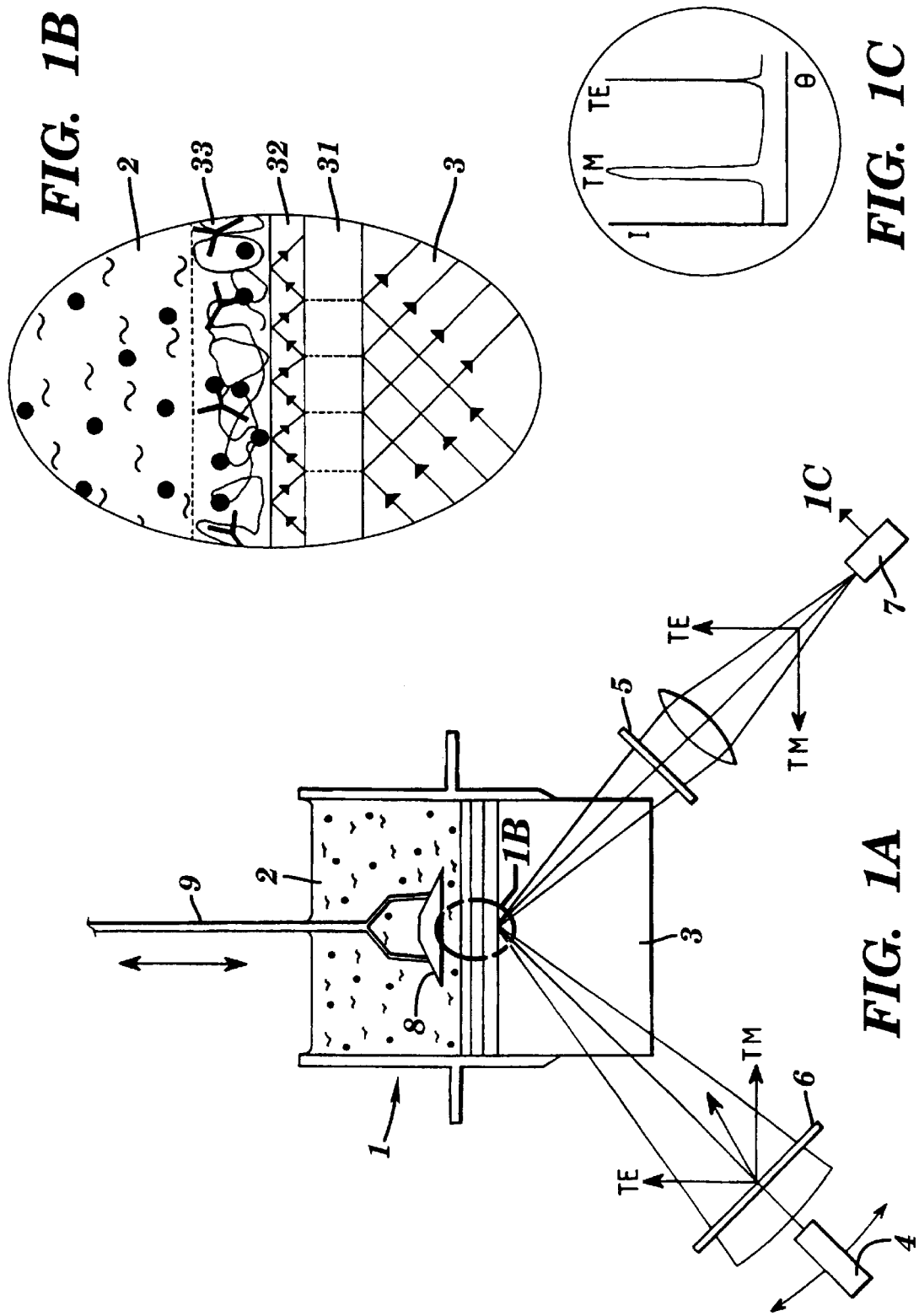

Referring first to FIG. 1, an analytical apparatus for the qualitative or quantitative determination of a biochemical analyte is based on the principle of frustrated total reflection. The apparatus comprises a sample cuvette 1 which defines a sample chamber 2. The base of the chamber 2 is a glass block 3, the upper surface of which is coated with several layers of material.

As shown in the enlarged portion of FIG. 1, the first layer applied to the surface of the block 3 is a relatively low refractive index layer 31 of silica with a thickness of approximately 500 nm. The second layer 32 is relatively high refractive index hafnia, of thickness approximately 100 nm. The hafnia layer is in turn coated with a layer of dextran 33 within which antibodies or other biomolecules are immobilised in known fashion.

The multilayer structure at the upper surface of the block 3 constitutes an FTR biosensor. The interface between the block 3 and the silica layer 31 is irradiated with light from a laser light source 4, which can be moved such that the angle of incidence of the light can be varied over a certain range. The hafnia layer 32 acts as a resonant cavity and at a certain angle of incidence of the light the evanescent field created by reflection at the interface between the block 3 and the silica layer 31 is coupled into the hafnia layer 32. The angle at which resonance occurs depends on the refractive index in the vicinity of the hafnia layer 32 and this is modified by interaction between the immobilised antibodies and analyte molecules (represented in FIG. 1 by solid black dots) in a sample which is introduced into the sample chamber 2.

Movement of the laser light source 4 over a range of angles is carried out as described in our International Patent Application No WO 93/14391. A polariser 6 is interposed between the light source 4 and the block 3, and is arranged such that the light incident on the block 3 has approximately equal TE (transverse electric) and TM (transverse magnetic) components. An analyser 5 is disposed between the block 3 and a detector 7 such that reflected light reaches the detector 7 only when resonance occurs. FIG. 1 shows a typical plot of measured light intensity I versus angle of incidence $\theta$. There are two resonant angles: one for TM-polarised light and the other for TE-polarised light.

The sample contained within the sample chamber 2 is stirred by a stirrer element 8 mounted on the end of a stirrer shaft 9. The shaft extends into the chamber 2 and, in used, the element 8 reciprocates along an axis perpendicular to the surface of the block 3, as shown by the double-headed arrow in FIG. 1.

Figure 2:
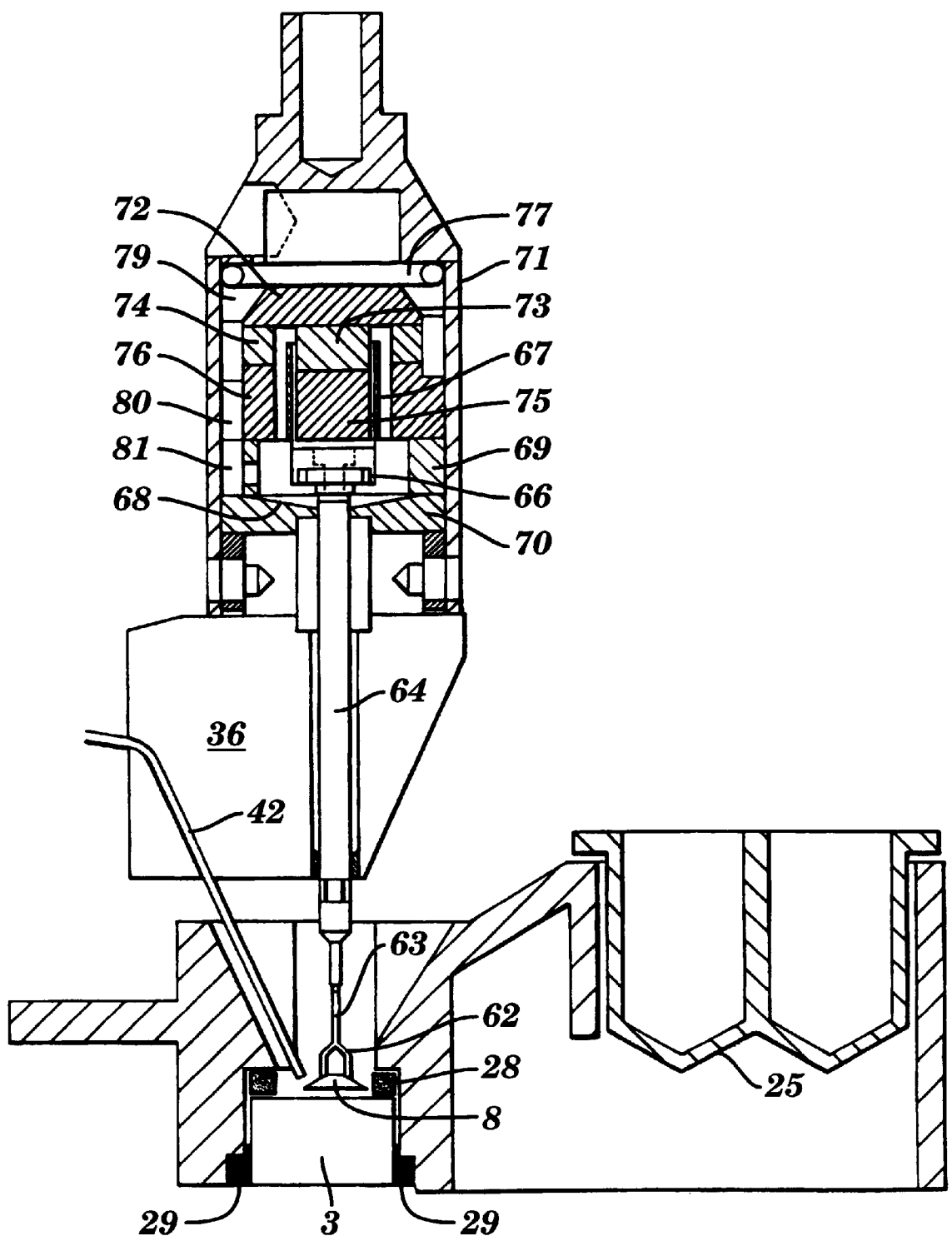
FIG. 2 is sectional side view of a sample cuvette and stirring mechanism forming part of the apparatus of FIG. 1.
Figure 3:
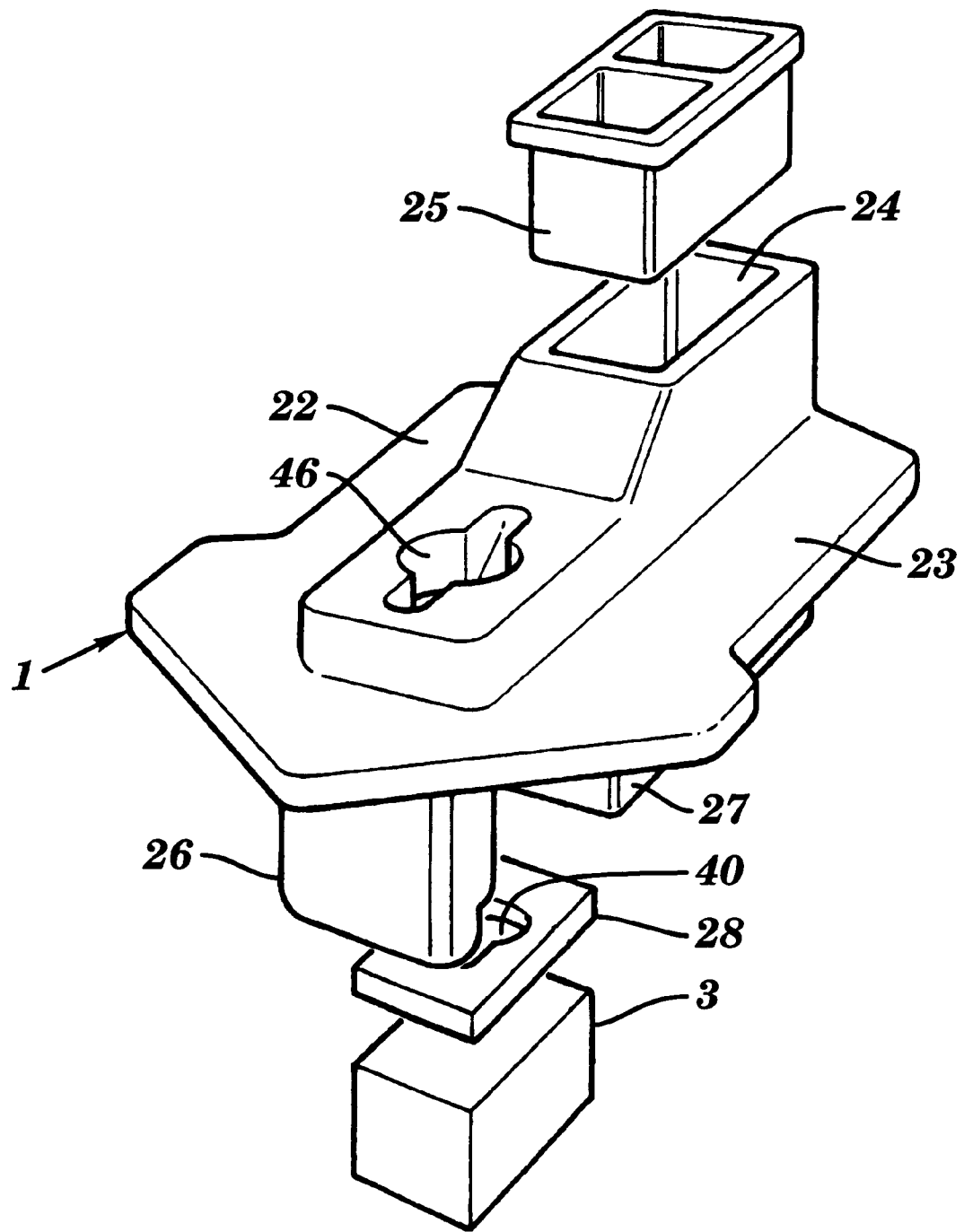
FIG. 3 is an exploded perspective view of the sample cuvette of FIG. 2.
Figure 4:
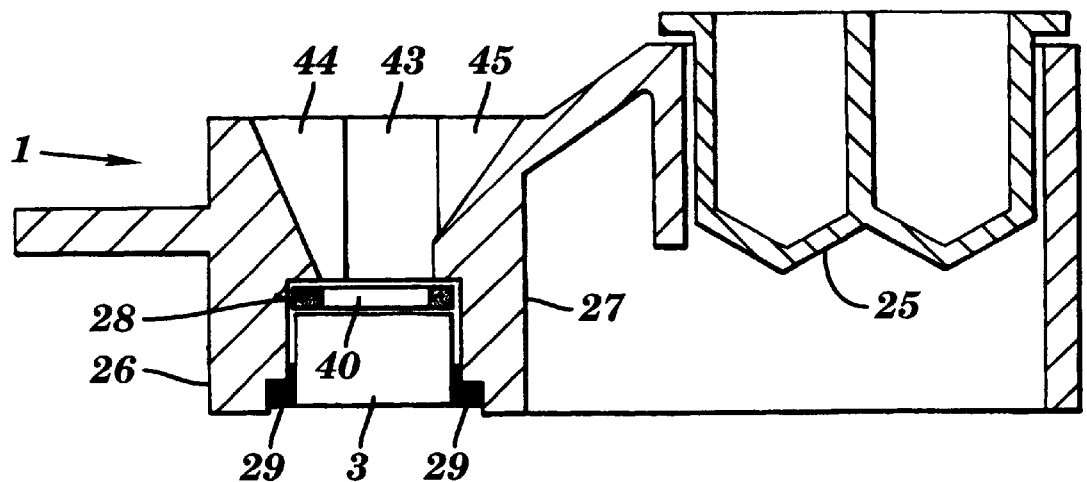
FIG. 4 is a sectional side view of the sample cuvette of FIG. 3.

The sample cuvette 1 and stirrer mechanism are shown in greater detail in FIG. 2, and the cuvette 1 also in FIGS. 3 and 4.

Referring next to FIG. 3, the sample cuvette 1 comprises an aluminium body produced by pressure die-casting. The body has a surface coating of deposited electroless nickel. The cuvette 1 is formed with laterally extending wings 22,23 which, in use, serve to support the cuvette 1 and provide for good thermal contact between the cuvette 1 and the adjacent surfaces of the measuring apparatus.

The cuvette 1 includes a recess 24 which receives a twin sample well 25. The well 25 is used for the storage of analytical reagents such as buffer solutions.

A pair of downwardly-depending limbs 26,27 receive a moulded silicone rubber gasket 28 and the glass block 3, the upper surface of which is coated as described above. The block 3 is held in place by uv-cured adhesive 29 applied around its base.

The silicone gasket 28 defines a sample compartment 40 with a volume of approximately 250 $\mu$l. Access to the compartment 40 is via a well 46 formed in the top of the body 21. The well 46 comprises a central portion 43 of circular cross-section and two diametrically opposed extension channels 44,45 (see FIG. 4).

In an alternative embodiment, the gasket 28 may be omitted and the block 3 secured directly to the underside of the cuvette 1 between the limbs 26,27. The sample compartment is then defined by the lower region of the well 46.

Figure 5:
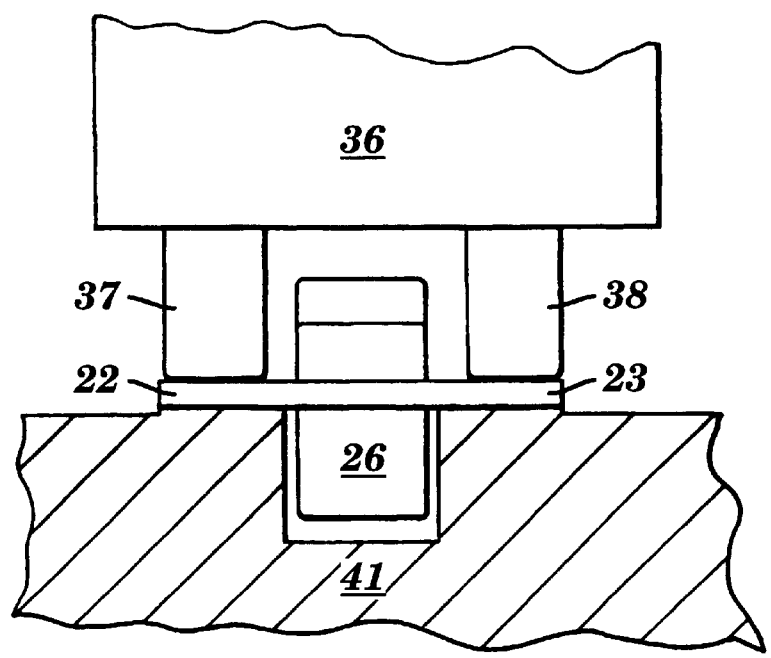
FIG. 5 is a schematic end view of the sample cuvette of FIG. 3, showing how the cuvette is clamped in position.

As can be seen from FIG. 5, when the cuvette 1 is positioned on the measuring apparatus, a clamping block 36 acts through two downwardly-depending members 37,38 on the wings 22,23 to hold them against an aluminium block 41 which forms part of the apparatus.

In addition to clamping the cuvette 1 in position, the block 36 also houses and supports the stirrer mechanism.

Figure 6:
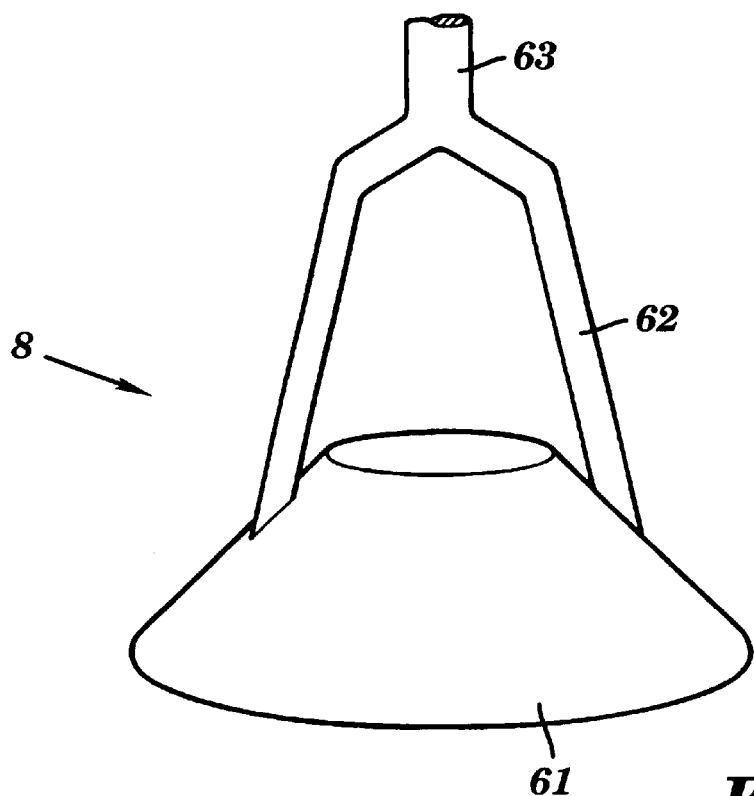
FIG. 6 is a perspective view of a stirrer element forming part of the mechanism of FIG. 2.

Referring now to FIG. 6, the stirrer element 8 comprises a 120° frusto-conical plate 61, formed by deformation of a 3.5 mm diameter stainless steel disc with a 1.1 mm diameter central aperture. The plate 61 is connected by a stirrup 62, formed from 0.25 mm thickness stainless steel sheet, to a lower drive shaft 63. The stirrup 62 is spot-welded to both the plate 61 and the lower drive shaft 63.

Referring once again to FIG. 2, the lower drive shaft 63 has a diameter, at the point where it is connected to the stirrup 62, of 0.5 mm. At its upper end, the lower drive shaft 63 is broadened to a diameter of 2 mm. The lower drive shaft 63 threadedly engages the lower end of an upper drive shaft 64 which extends through a bore in the clamping block 36, and through a retaining plate 70 into an upper motor unit.

The upper drive shaft 64 is connected at its upper end to a coil former assembly comprising a coil mounting plate 66 and an upwardly extending, hollow, cylindrical coil former 67. A disc spring 68 is captivated between the coil mounting plate 66 and the upper drive shaft 64, and is held at its periphery between the retaining plate 70 and a connection guide 69.

To prevent twisting of the disc spring 68 and coil former assembly when the lower drive shaft 63 is threadedly engaged with or disengaged from the upper drive shaft 64, the upper portion of the upper drive shaft 64 has a square cross-section, corresponding to the shape of the central aperture in the retaining plate 70.

The retaining plate 70 and connection guide 69 fit closely within an upper motor case carriage 71, and retain a magnet assembly and O-ring 77. The magnet assembly comprises a backing plate 72, to the underside of which are fixed, by adhesive, a central button magnet 73 and an outer ring magnet 74. A soft iron inner core 75 is fixed to the underside of the button magnet 73 and an annular soft iron outer core 76 is fixed by adhesive to the underside of the ring magnet 74.

The coil former 67, on which the coil is wound, is freely mounted about the button magnet 73/soft iron inner core 75. The backing plate 72, the soft iron outer core 76 and the connection guide 69 are provided with peripheral slots 79,80,81 through which flexible connections are led to the coil.

In use, an alternating current of frequency 120 Hz is applied to the coil. This causes the coil former assembly, and hence the stirrer element 8, to reciprocate along the axis of the upper and lower drive shafts 63,64 through an amplitude of ±0.3 mm. The rest position of the stirrer element 8 is approximately 0.5 mm above the coated surface of the block 3, and thus the stirrer element 8 oscillates between extreme positions 0.2 mm and 0.8 mm above that surface.

A sample is injected into the sample compartment 40 by means of a syringe inserted into one of the extension channels 45. The other extension channel 44 receives a suction needle 42 which is used to remove sample from the compartment 40 after a measurement is complete.

The cuvette 1 is positioned on the supporting aluminium block 41. Sample is introduced into the compartment 40 either before or after the cuvette is so positioned. The block 3 is irradiated with light from the light source 4, such that the light is reflected towards the detector 7. The angle of incidence of the light is varied and the angle at which resonance occurs (detected as a peak in the light reaching the detector) is determined.

The stirring of the sample by the stirrer element 8 during measurement ensures homogenisation of the sample and prevents any spurious effects due to transport phenomena within the sample. The good thermal contact between the wings 22,23 of the cuvette 1 and the supporting block 41 ensures rapid thermal equilibration, as does the fact that the thermal capacity of the cuvette 1 is very much greater than that of the sample.

Figure 7:
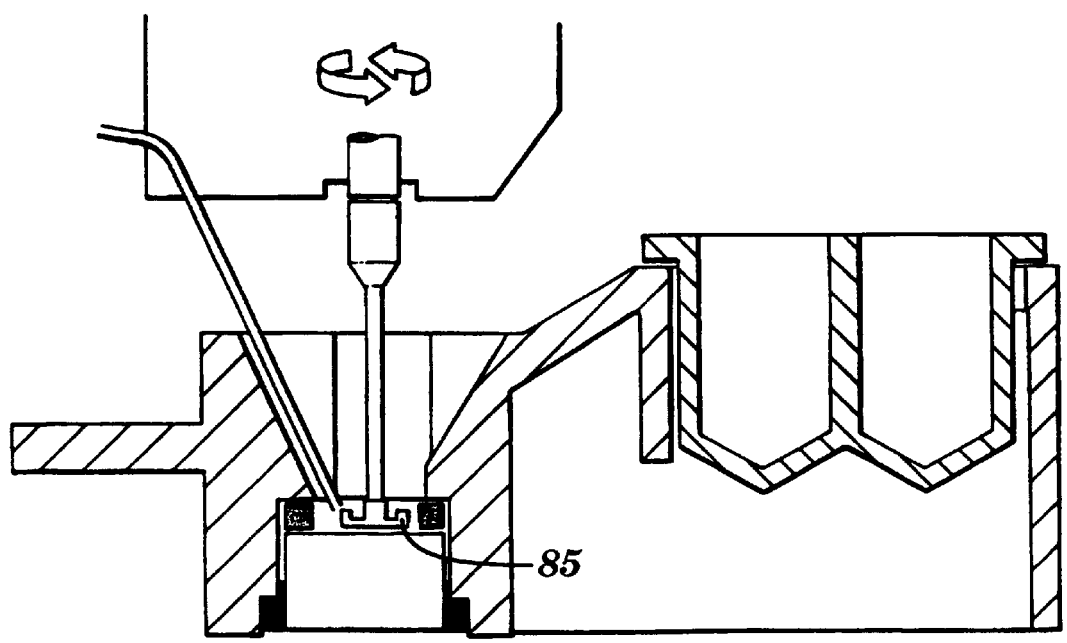
FIG. 7 is a view similar to FIG. 2 of an analytical apparatus according to the invention incorporating a second form of stirrer mechanism.
Figure 8:
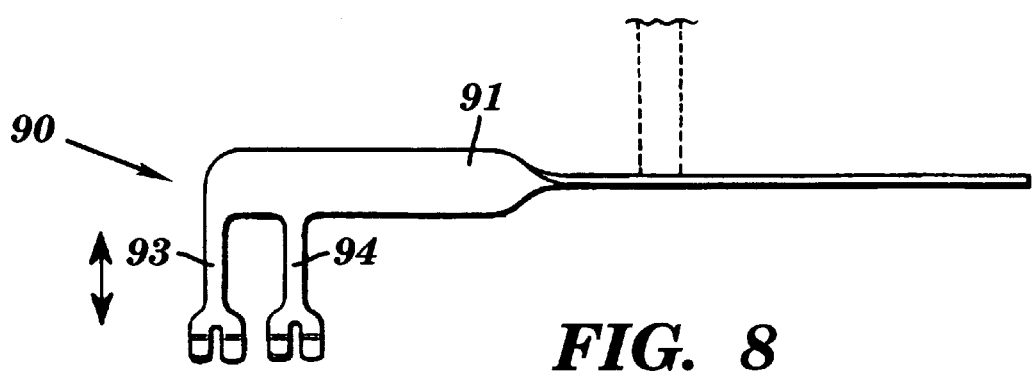
FIG. 8 is a side view of a stirrer element for use in a third embodiment of an analytical apparatus according to the invention.
Figure 9:
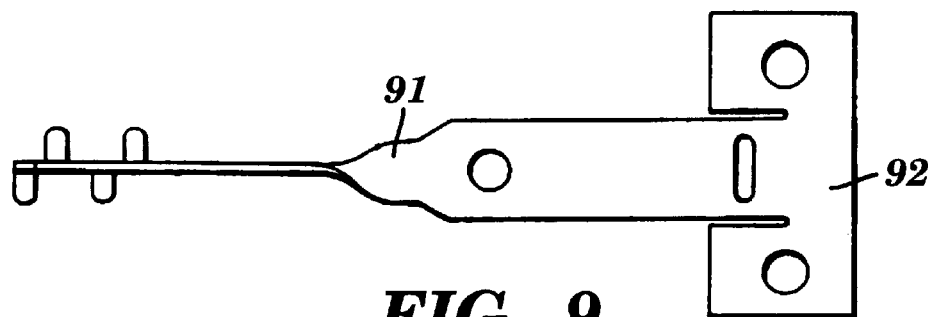
FIG. 9 is a plan view of the stirrer element of FIG. 8.
Figure 10:
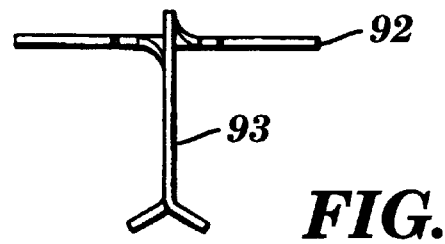
FIG. 10 is an end view of the stirrer element of FIG. 8.

FIG. 7 shows an arrangement which is generally very similar to that of FIG. 2, save that the stirrer element 85 is rotated rather than vibrated.

Finally, FIGS. 8 to 11 show a form of stirring element 90 which is intended for use in an apparatus comprising two adjacent sample chambers. The element 90 comprises a beam 91 which is fixed at one end by means of a flange 92. The beam 91 is, in use, fixed to the end of a reciprocating stirrer shaft (shown by the broken line in FIG. 8) such that the free end of the beam 91 vibrates, as shown by the double-headed arrow in FIG. 8. The stirrer shaft is driven by an electromagnetic mechanism similar to that shown in FIG. 2. The free end of the beam 91 is formed with downwardly depending limbs 93,94, the ends of which are forked and splayed. The limbs 93,94 extend, in use, into two adjacent sample compartments in a cuvette generally similar to that described above.

Figure 11:
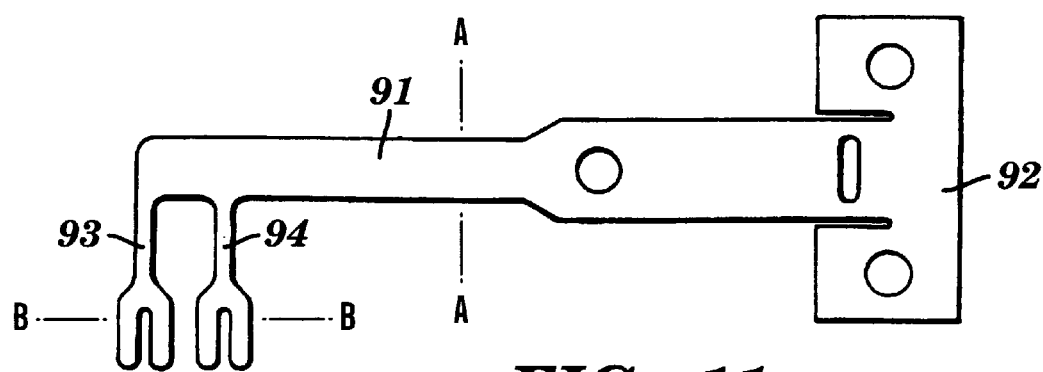
FIG. 11 is a plan view of a blank from which the stirrer element of FIG. 8 is formed.

The stirrer element 91 is formed from the blank shown in FIG. 11, by twisting of the beam 91 in the region of the line A—A and splaying of the forked ends of the limbs 93,94 along the line B—B.

What is claimed is:
1. A sample cuvette comprising:
   a body of material with high thermal conductivity;
   a sample chamber defined within said body and having a base;
   a biosensor device having a sensitive surface incorporated within said base;
   wherein said body is provided with integrally formed wings or flanges, formed of said material with high thermal conductivity, by which the cuvette may be held in intimate thermal contact with a support.
2. A sample cuvette as claimed in claim 1, wherein said material with high thermal conductivity is a metal.
3. A sample cuvette as claimed in claim 2, wherein said metal is aluminum.
4. A sample cuvette as claimed in claim 1, wherein said body is coated with a coating of electroless nickel, a fluorocarbon, or a silicon lacquer.
5. A sample cuvette as claimed in claim 4, wherein said coating has a thickness of the order of 25 $\mu$m.
6. A sample cuvette as claimed in claim 1, wherein said sample chamber has a volume of less than 500 $\mu$l.
7. A sample cuvette as claimed in claim 6, wherein the volume of said sample chamber is 100–300 $\mu$l.
8. A sample cuvette as claimed in claim 1, which includes one or more reserve fluid wells for maintaining a supply of sample or analytical reagents at the same temperature as the temperature of material contained within said sample chamber.
9. Analytical apparatus comprising a support and a sample cuvette as claimed in claim 1.
10. Analytical apparatus as claimed in claim 9, further comprising clamping means for holding said sample cuvette in contact with said support.
11. A sample cuvette comprising:
   a body of metal having high thermal conductivity;
   a sample chamber defined within said body and having a base;
   a biosensor device having a sensitive surface incorporated within said base;
   wherein said body is provided with integrally formed wings or flanges by which the cuvette may be held in intimate thermal contact with a support.
12. A sample cuvette as claimed in claim 11, wherein said metal is aluminum.
13. A sample cuvette as claimed in claim 11, wherein said body is coated with a coating of electroless nickel, a fluorocarbon, or a silicon lacquer.
14. A sample cuvette as claimed in claim 13, wherein said coating has a thickness of the order of 25 $\mu$m.
15. A sample cuvette as claimed in claim 11, wherein said sample chamber has a volume of less than 500 $\mu$l.
16. A sample cuvette as claimed in claim 15, wherein the volume of said sample chamber is 100–300 $\mu$l.
17. A sample cuvette as claimed in claim 11, which includes one or more reserve fluid wells for maintaining a supply of sample or analytical reagents at the same temperature as the temperature of material contained within said sample chamber.
18. Analytical apparatus comprising a support and a sample cuvette as claimed in claim 11.
19. Analytical apparatus as claimed in claim 18, further comprising clamping means for holding said sample cuvette in contact with said support.
20. A sample cuvette as claimed in claim 11, wherein said wings or flanges are formed of said metal having high thermal conductivity.

* * * * *